(12) United States Patent
Kwirandt

(10) Patent No.: US 6,654,116 B1
(45) Date of Patent: Nov. 25, 2003

(54) DEVICE AND METHOD OF OPTICAL INSPECTION OF OPEN BEVERAGE CONTAINERS

(75) Inventor: Rainer Kwirandt, Obertraubling (DE)

(73) Assignee: Krones AG Hermann Kronseder, Neutraubling (DE)

(*) Notice: Subject to any disclaimer, the term of this patent is extended or adjusted under 35 U.S.C. 154(b) by 72 days.

(21) Appl. No.: 09/634,508

(22) Filed: Aug. 9, 2000

(30) Foreign Application Priority Data

Aug. 25, 1999 (DE) .......................................... 199 40 363

(51) Int. Cl.⁷ .............................................. G01N 21/90
(52) U.S. Cl. ................................... 356/240.1; 209/524
(58) Field of Search .................. 356/240.1; 250/233 B; 209/524

(56) References Cited

U.S. PATENT DOCUMENTS

| | | | |
|---|---|---|---|
| 4,682,023 A | 7/1987 | Yoshida | |
| 4,758,084 A | 7/1988 | Tokumi et al. | |
| 4,924,107 A | 5/1990 | Tucker | |
| 5,030,823 A | 7/1991 | Obdeijn | |
| 5,220,400 A | 6/1993 | Anderson et al. | |
| 5,585,917 A | 12/1996 | Woite et al. | |
| 5,699,152 A | * 12/1997 | Fedor et al. | 356/240.1 |
| 5,822,056 A | * 10/1998 | Waters et al. | 356/240.1 |
| 5,912,776 A | * 6/1999 | Yaginuma | 356/240.1 |

FOREIGN PATENT DOCUMENTS

| | | |
|---|---|---|
| DE | 4408948 | 2/1998 |
| EP | 63760 | 3/1982 |
| EP | 362679 | 4/1990 |
| EP | A1 0371546 | 6/1990 |
| EP | 610956 | 8/1994 |
| GB | 2318635 | 4/1998 |
| WO | WO91/06846 | 5/1991 |
| WO | WO96/31768 | 10/1996 |
| WO | WO 98/19150 | 5/1998 |
| WO | WO98/19150 | 5/1998 |

* cited by examiner

Primary Examiner—Richard A. Rosenberger

(57) ABSTRACT

A device (V) for optical inspection of open beverage cans (D) having a light source (Q, Q') positioned outside the can, a reflector (R) for reflected light from the inside of the can, arranged between the light source and the opening in the can, a camera (E) which is alighed with the reflector, and an optical device (P) with which the light (11) from the light source (Q, Q') can be projected from above through the opening (4) in the can directly onto the bottom (B) of the can, whereby the can collar (K) can be illuminated from the bottom (B) of the can on the inside. In this method, the light is bundled and directed through the narrow section of the reflector, then expanded after the reflector and projected directly onto the can bottom (B) centrally as the light spot (13, 13') displacing the light source (Q, Q') into the can in order to illuminate the inside wall of the collar from beneath from the light spot and to image it by the reflected light.

14 Claims, 1 Drawing Sheet

DEVICE AND METHOD OF OPTICAL INSPECTION OF OPEN BEVERAGE CONTAINERS

FIELD OF THE INVENTION

This invention relates to a device characterized in the definition of the species of claim 1 and a method for accomplishing the same.

BACKGROUND OF THE INVENTION

Optical inspection of open beverage cans is performed, for example, in the bottling industry to sort out damaged, defective and/or soiled cans.

With the device of this type known from International Patent WO 96/31768, the collar on the inside of the can is illuminated obliquely from the outside above and imaged in a camera whose its optical axis is aligned with the axis of the can by using a reflector so that the path of the curve of the collar appears elongated. At the same time, the edge flange of the can is imaged separately. At another station of this device, the illuminated bottom of the can is imaged and examined together with an image of the inside lower wall area of the can. The light source is a truncated conical arrangement of LEDs above and outside the reflector.

Beam splitter mirrors and cameras arranged at the side are used for imaging the bottom and flange areas. Only a small portion of the incident light is reflected to the reflector. The inside surface of the collar facing outward and down cannot be imaged satisfactorily because a large portion of the light directed inward at the inside wall of the collar from outside and above at an inclination is reflected downward and is consumed by multiple reflection.

With the device known from International Patent WO 91/06846, the can having a bottom with a concave curvature is illuminated from the outside by means of a light source with a dome-shaped three-dimensional LED arrangement. A fisheye lens is arranged inside the light source. The various sections in the interior of the can are illuminated at different intensities, with the lighting intensity at the bottom of the can being lower than that on the inside wall of the collar of the can because of multiple reflection. Beams of light directed downward at an inclination are reflected repeatedly except for the bottom of the can. Beams of light directed vertically strike the bottom of the can directly. Direct light as well as reflected light striking the bottom of the can is reflected axially outward, with the light that is reflected outward and up at an angle from the inside bottom being brought to the lens by multiple reflections and over the inside wall of the collar. Therefor, a substantial portion of the incident light is lost. The image of the inside wall of the collar is not sufficiently informative. The light goes astray in the interior of the can, is absorbed to a great extent and produces such diffuse lighting of defects that they are hardly perceptible in the image.

SUMMARY OF THE INVENTION

With the device known from International Patent WO 98/19150 for the inspection of bottles, opaque bottles are illuminated from the outside to inspect the mouth sealing area and the outer thread area of the mouth surface. The reflected light is thrown by a pyramid-shaped or a round, dish-shaped optical conical reflector onto the lens of the camera. The conical reflector operates according to the optical principal of total reflection so that it advantageously does not need any opaque reflector surfaces that would be susceptible to damage.

The object of the present invention is to provide a device of the type defined initially and a method with which an informational image of the inside wall area of the collar that is critical with regard to damage and/or soiling is possible.

With this device, the light source is displaced virtually with this optical device to the bottom of the can through the opening in the can without any mentionable loss of light on the path to the bottom of the can for lighting the inside wall of the can. With the light source virtually displaced to the bottom of the can, the inside wall of the collar is illuminated intensely and uniformly from beneath thanks to the reflective properties of the bottom of the can in order to create an informational image from the reflected light coming from the inside wall of the collar. In this way, a considerable portion of the light can be utilized. Defects, soiling or residues on the collar can be detected easily and quickly; this is especially important for a bottling instillation operating at a high speed in order to sort out any damaged or soiled cans before they can cause a production interruption, or at least to be able to mark such a can.

According to the present invention, the procedure followed is that first no mentionable attention is devoted to the actual section of the can to be imaged, namely the inside wall of the collar, when it is illuminated but instead essentially the incident light directed into the can from the outside is bundled and passes through the narrow section of the reflector and then is directed through the opening in the can only at the bottom of the can. In order to be able to produce a uniformly illuminated and geometrically precisely defined light spot on the bottom of the can, by means of which the inside wall of the collar which is inclined radially inward can be illuminated effectively from beneath, the light which is at first bundled is then expanded accordingly. The reflected light coming from beneath and reflected on the inside wall of the collar reaches the camera, which then produces an informational image of the critical inside wall area of the collar thanks to an illumination quality similar to that which would be achieved if the light source were positioned on the bottom of the can.

Preferably a central circular or annular light spot is produced on the bottom of the can, representing the light source, and it should not be any larger than the outside diameter of the bottom of the can. In order to be able to utilize the largest possible cross section of the reflector with regard to a high reflection light yield, only a small opening in the reflector is used for illuminating the bottom of the can with bundled light, but this is not expanded optically after the narrow section to image a uniformly illuminated light spot on the bottom of the can which has a concave curvature and to utilize its reflective properties.

To achieve a sufficient light intensity even through a very small narrow section, beam shaping means should be provided between the light source and the narrow section for bundling and/or adjusting the beam outline to the outline of the bottom of the can.

If light of a traditional light source were bundled so that it could easily pass through a hole 5 to 10 mm in size, the light intensity that could be achieved would be too weak. However, if the light intensity of the traditional light source is strong enough, the light will diverge greatly and will strike the optical components of the reflector, thus producing reflection and strong overexposure and/or ghost images. Therefore, the light source is preferably a laser, in particular a semiconductor laser which delivers a bundled beam of light that passes through the narrow section(s) of the reflector without any loss. A collimator lens should be provided with the laser light source to bundle or focus the laser light beam. Then a cylindrical lens is expedient in order to change the astigmatic beam contour into a round contour which is used in the light spot on the bottom of the can. In focusing, the focal point is located within the range between the cylindrical lens and the interior of the reflector, depending on the setting. The narrow section may be a circular orifice with a diameter of 5 to 10 mm, for example.

Since modern laser light sources are very small, it would be conceivable to position a laser light source centrally above or in the narrow section.

However, the laser light source is preferably positioned at the side outside the path of the reflected light of the reflector directed toward the camera, and the bundled and focused laser light beam is reflected through a deflecting mirror through the narrow section.

It may be fundamentally advantageous to use or design the laser light source positioned centrally or the reflecting mirror as shading elements in order to avoid glare at the middle of the image that would interfere with the analysis of the image.

To widen the bundled and focused beam appropriately, a scattering lens should be provided downstream from the narrow section, preferably inside the reflector.

If a deflecting mirror is provided, it can easily be mounted on the reflector with a mount above an orifice of the reflector which defines the narrow section and optionally adjusted there.

The reflector, preferably a conical reflector, should preferably be covered by a protective glass to keep out soiling. The scattering lens can be mounted easily on the protected safety glass. The lens and the deflecting mirror, however, may also be mounted on a hollow tube (mirror on the upper end, lens on the lower end) which is mounted in the orifice of the reflector and has an inlet opening for the laser beam at the side next to the deflecting mirror.

According to this invention, the bundled and shaped laser light beam is expanded optically only downstream from the narrow section in such a way as to yield a uniformly illuminated light spot of a certain size and shape centrally on the bottom of the can. Since the widening takes place only downstream from the narrow section, reflections and severe overexposure and/or ghost images in the path of the beam to the narrow section can be avoided.

BRIEF DESCRIPTION OF THE DRAWING

One embodiment of the object of this invention is illustrated in FIG. 1 of the drawings, where one detailed variant is shown with dotted lines.

DETAILED DESCRIPTION OF THE PREFERRED EMBODIMENT

Figure 1:
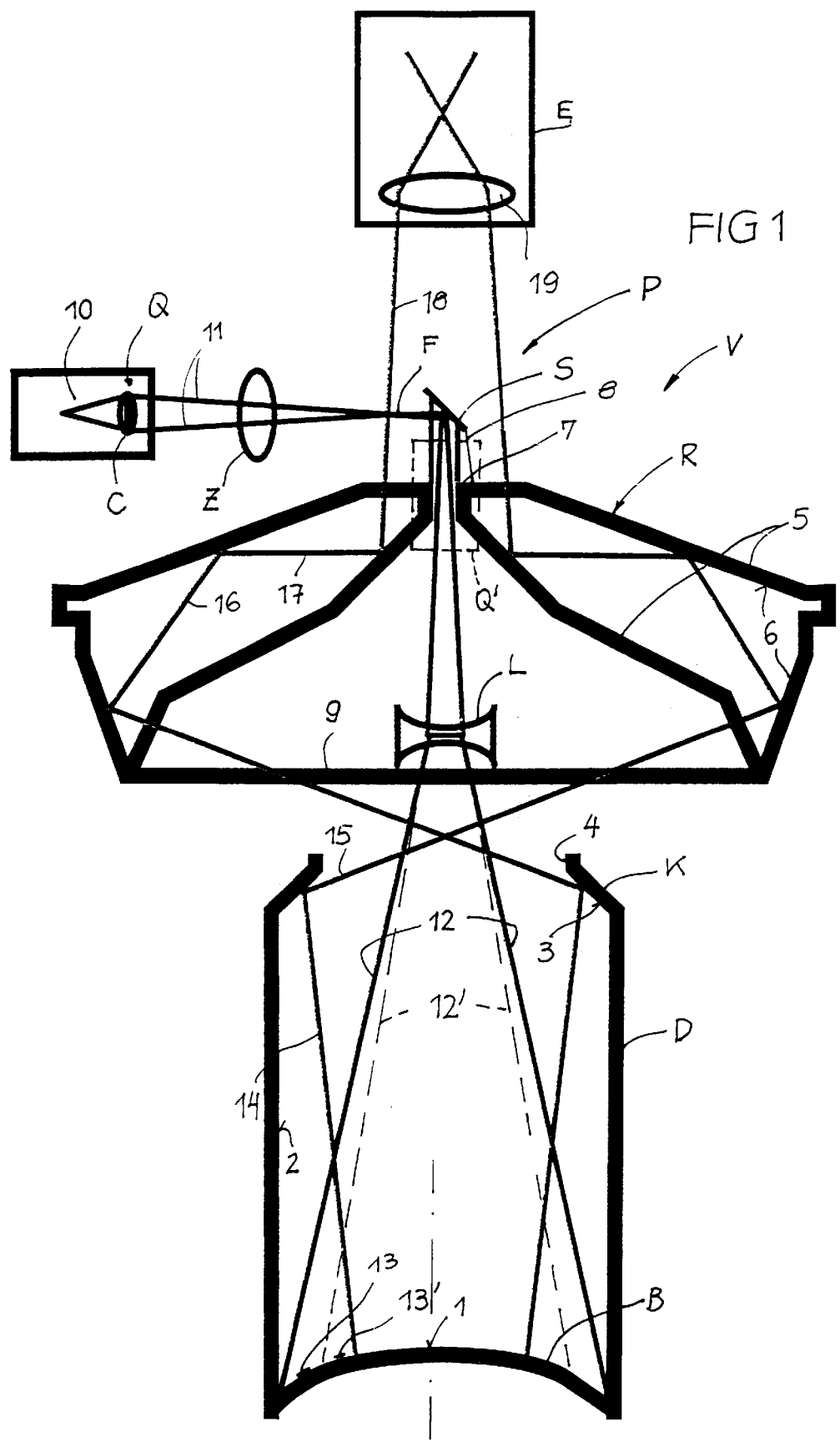

A device V for sequential optical inspection of open beverage cans D, e.g., in a bottling installation (not shown), has at least one electronic camera E whose optical axis corresponds to the center axis of can D at the moment when the image is recorded with the embodiment illustrated in FIG. 1, and it is positioned above can D to be inspected. Between camera E and can D there is a reflector R. Between camera E and reflector R, a light source Q is positioned laterally outside the path of the beam of the reflected light from reflector R to camera E and is directed at a deflecting mirror S which is arranged on reflector R above and belongs with an optical device indicated as P in general. The light source Q may be, for example, a laser light source 10, e.g., a semiconductor laser which has a collimator lens C for bundling the light 11 with a cylindrical lens Z provided downstream from it to convert the astigmatic outline of line 11 into a round shape. The lenses C and Z form first beam shaping agents for the light 11 which serves to illuminate the interior of can D.

As another beam shaping agent L, a scattering lens which is preferably arranged on a safety glass 9 of reflector R is provided in reflector R which is preferably a conical reflector with totally reflecting surfaces 6 in a housing 5 or a transparent glass or plastic body.

The can D has a reflecting can bottom B which has an inward curvature as is conventional with beverage cans in order to achieve a compressive strength and has a collar K at the top which turned inward at an angle and leads to an upper opening 4 into which, after the can is filled, a top is inserted and secured by flange connection.

The surface of can bottom B, which is labeled as 1, is reflective, as stated above, as is optionally also the inside wall of the body of the can which is labeled as 2 and the inclined inside wall 3 of collar K or the shoulder area. At the center of reflector R, a narrow section 7 is provided, e.g., an opening 5 to 10 mm in size through which the light 11 coming from light source Q is reflected downward by deflecting mirror S. The light 11 is focused by the beam shaping agents C, Z, with the focal point F being located just in front of the deflecting mirror S or at least within the range between the cylinder sleeve Z and the scattering lens L.

The incident light 11 is expanded by the scattering lens L to form a cone 12 of light which is directed from above directly onto the can bottom B, where it forms a uniformly bright central light spot 13. Thus, the light source Q is displaced to can bottom B by means of optical device P. The light spot 13 should be circular and should preferably be no larger than the can bottom B. It may optionally even be smaller than this (indicated with dotted lines at 13'). Light 14 is reflected upward from can bottom B or the light source Q, which is displaced into light spot 13 or 13' and is reflected upward and at an angle outward toward the inside wall 3 of collar K and from there at an angle outward (indicated at 15) onto reflector R. The reflected light is diverted at the totally reflecting surfaces 6, as indicated by 16 and 17, and then finally strikes a lens 19 of camera E in a bundled reflected light beam 8.

Deflecting mirror S may be mounted on the top side of reflector R with a mount 8. The scattering lens L is preferably glued to the safety glass 9. A cover which optionally also supports the beam shaping elements C, Z may be provided for protection for light 11 from light source Q.

Light source Q' which is indicated with dotted lines may be positioned either directly above the narrow section 7 or inside the narrow section 7. Preferably the deflecting mirror S or the centrally positioned light source Q' forms a shading element for the center of the light spot 13 or 13' which may also produce glare.

The narrow section may be an orifice with a diameter between 5 and 10 mm. This size is sufficient to achieve a sufficient light intensity by means of laser light source Q in light spot 13, 13' and to achieve a uniform illumination density.

Since the inside wall 3 of the collar K and the opening edge 4 are illuminated from beneath intensely and with little loss, a very informative image of these areas can be achieved in camera E, clearly illustrating the manufacturing induced damage to the collar or the edge of the opening or and swelling or residues (for example, by comparison with a reference image). The quality of the image can be optimized through the intensity of the laser light source Q, the position of the focal point F, the size of the light spot 13 or 13' on the can bottom B which is adjusted by means of the scattering lens L and the height of the reflector R, with the magnification of the camera image, the aperture setting, the exposure time and the like all playing a roll. The noise which increases with enlargement of the camera image is superimposed on speckle of the laser light. However, the speckle disappears if there is a slight movement of the can. To improve the image quality by washing the speckle, it may be expedient to perform the inspection of the can when it is moving slightly anyway. A light spot having a uniform brightness and located centrally on the bottom of the can has proven optimum for image quality, where the diameter of the light spot may be smaller than the outside diameter of the bottom of the can. A light spot larger in size than the outside diameter of the bottom will also light up the inside wall of the can. However, because of increasing diffusion, this can lead to an unwanted weakening of the light.

It is advantageous if the laser light source emits light at a minimum power of 30 mW. However, an increase would be possible by using pulsed operation.

To inspect the cans, they can be passed beneath the reflector continuously at a high speed in a single file row by a conveyer means such as a conveyor belt, with the cans being illuminated and the images recorded when the vertical axis of a can is essentially aligned with the optical axis of the camera. An analyzer device performs an image analysis, supplying a signal automatically when a defective can is detected in order to sort out that can automatically.

The above mentioned narrow section 7 in the reflector R need not necessarily be imaged as a boar hole or a cavity as illustrated in the accompanying drawing, but instead it may also be formed by a zone with parallel incident and exit surfaces aligned at a right angle to the beam of light when using a reflector made of a transparent material. Instead of a conical reflector R, another suitable optical means such as suitably positioned optical fibers or the like may be used.

In deviation from the embodiment described above, the position of the camera may be exchanged with the position of the laser light source if an annular deflecting mirror arranged at an inclination and having a central boar hole for the laser beam is used.

I claim:

1. A device (V) for optical inspection of beverage cans (D) having a bottom (B) and recessed collar (K), each having reflecting properties, comprising at least one laser light source (Q, Q') positioned outside the can for illuminating the inside of the can, a reflector (R) for reflected light from the inside of the can arranged between said laser light source and the opening in the can, a camera (E) which is connected to an analyzer device and is aligned with said reflector, and an optical device (P) with which light (11) from said laser light source (Q, Q') can be projected through the opening (4) in the can from above directly onto the bottom (B) of the can, for virtual displacement of said light source (Q, Q') to the bottom (B) of the can, and with which the collar (K) can be illuminated from the bottom (B) of the can on the inside, wherein said reflector (R) has a narrow section (7) for passage of the laser light (11), and beam shaping elements (L) for widening the light beam provided in the path of the beam of light downstream from said narrow section (7), and wherein said laser light source (10) is positioned laterally outside the path (18) of the reflected beam of said reflector (R) which is directed toward said camera (E), and a deflecting mirror (S) is arranged above an opening in said reflector (R) which defines said narrow section (7).

2. A device according to claim 1, and a central, approximately circular or annular light spot (13, 13') produced on the bottom (B) of the can by using said optical device (P) where the outside diameter of said light spot preferably corresponds at most to the outside diameter of the bottom of the can.

3. A device according to claim 1, wherein said reflector (R) has a narrow section (7) for passage of the light (11), and beam shaping elements (L) for widening the light beam provided in the path of the beam of light downstream from said narrow section (7).

4. A device according to claim 3, wherein said beam shaping element (C, Z) permits bundling and/or adjusting the outline of the light beam to the outline of the bottom (B) of the can and are provided between said light source (Q) and said narrow section (7).

5. A device according to claim 3, wherein said beam shaping element (L) is at least a scattering lens positioned downstream from said narrow/section (7).

6. A device according to claim 5, wherein said reflector faces the can (D) and is covered by a safety glass (9), and a scattering lens (L) is arranged on said safety glass.

7. A device according to claim 5, wherein said scattering lens is positioned inside said reflector(R).

8. A device according to claim 1, and a collimator lens (C) and at least one cylindrical lens (Z) are provided with said laser light source (10).

9. A device according to claim 8, and the collimator having a cylinder effect.

10. A device according to claim 1, wherein said deflecting mirror (S) forms a shading element for the central area of the light spot (13, 13').

11. A device according to claim 1, and wherein said laser light source (10) is a semiconductor laser.

12. A method of optical inspection of beverage cans that are open at the top, where the inside of the can is illuminated with light from at least one laser light source through the opening in the can, and an image of the inside wall of a collar of the can which is turned in at the top and is formed from the reflected light over a reflector comprising the following steps:

a) bundling and reflecting the laser light from the side into a narrow section (7) and passing the light through said light-permeable narrow section (7) of the reflector, b) expanding and projecting the light passing through the narrow section (7) centrally directly onto the bottom (B) of the can as a light spot (13, 13') which shifts the light source into the can, c) illuminating the inside wall (3) of the collar (K) from beneath by the light spot (13, 13'), d) reflecting the light (15) upward and outward from the inside wall (3) of the collar (K) from the reflector (R), which is a conical reflector, to an imaging camera (E).

13. A method according to claim 12, and bundling and shaping the laser light to expand it optically to a light spot of a size corresponding at most to the outside diameter of the bottom of the can (B).

14. A method according to claim 12, and focusing the laser light in the beam path upstream from the expanded portion.

* * * * *

UNITED STATES PATENT AND TRADEMARK OFFICE
CERTIFICATE OF CORRECTION

PATENT NO.      : 6,654,116 B2
DATED           : November 25, 2003
INVENTOR(S)     : Rainer Kwirandt It is certified that error appears in the above-identified patent and that said Letters Patent is hereby corrected as shown below:

Title page,
Item [73], Assignee, replace "Krones AG Hermann Kronseder" with
-- Krones AG Hermann Kronseder Maschinenfabrik --
Item [57], ABSTRACT,
Line 5, replace "alighed" with -- aligned --

Column 6,
Line 23, replace "narrow/section" with -- narrow section --
Line 44, replace "reflector" with -- reflector, --
Line 63, replace "claim 12," with -- claim 12 --

Signed and Sealed this

Twenty-third Day of March, 2004

JON W. DUDAS
*Acting Director of the United States Patent and Trademark Office*